(12) United States Patent
Takeda et al.

(10) Patent No.: US 12,215,964 B2
(45) Date of Patent: Feb. 4, 2025

(54) HEIGHT ESTIMATION METHOD, HEIGHT ESTIMATION APPARATUS, AND PROGRAM

(71) Applicant: NIPPON TELEGRAPH AND TELEPHONE CORPORATION, Tokyo (JP)

(72) Inventors: Toshiaki Takeda, Musashino (JP); Dan Mikami, Musashino (JP); Yoshinori Kusachi, Musashino (JP)

(73) Assignee: NIPPON TELEGRAPH AND TELEPHONE CORPORATION, Tokyo (JP)

( * ) Notice: Subject to any disclaimer, the term of this patent is extended or adjusted under 35 U.S.C. 154(b) by 361 days.

(21) Appl. No.: 17/800,588

(22) PCT Filed: Feb. 20, 2020

(86) PCT No.: PCT/JP2020/006749
§ 371 (c)(1),
(2) Date: Aug. 18, 2022

(87) PCT Pub. No.: WO2021/166148
PCT Pub. Date: Aug. 26, 2021

(65) Prior Publication Data
US 2023/0071054 A1    Mar. 9, 2023

(51) Int. Cl.
*G01B 11/02*  (2006.01)
*G06T 7/73*  (2017.01)

(52) U.S. Cl.
CPC .............. *G01B 11/02* (2013.01); *G06T 7/73* (2017.01); *G06T 2207/30196* (2013.01)

(58) Field of Classification Search
CPC .............. G01B 11/02; G01B 11/022; G06T 2207/30196; G06T 7/73; G06T 7/60
See application file for complete search history.

(56) References Cited

U.S. PATENT DOCUMENTS

2022/0138458 A1*  5/2022  Shibata .................. G06T 7/73
382/103

OTHER PUBLICATIONS

Zhe Cao et al., Realtime Multi-Person 2D Pose Estimation using Part Affinity Fields, 2017 IEEE Conference on Computer Vision and Pattern Recognition (CVPR), Jul. 21, 2017.

(Continued)

*Primary Examiner* — Manuchehr Rahmjoo
(74) *Attorney, Agent, or Firm* — Harness, Dickey & Pierce, P.L.C.

(57) ABSTRACT

A height estimation method performed by a height estimation apparatus includes a first feature point extraction step of extracting a feature point coordinate, a first coordinate estimation step of estimating a coordinate of a first subject frame, a pre-generation step of deriving a height of the first subject frame and generating a distance addition pattern and a correction coefficient for an individual missing pattern, a second feature point extraction step of extracting a feature point coordinate from a second input image, a second coordinate estimation step of estimating a coordinate of a second subject frame and estimating a coordinate of an object frame, a subject data selection step of selecting the individual missing pattern and the correction coefficient in accordance with the feature point coordinate, an object data selection step of selecting an object height, and a height estimation step of adding up a distance between a feature point coordinate and another feature point coordinate extracted in accordance with the missing pattern and deriving an estimated value of a height of the subject in accordance with a result of adding up the distance, the correction coefficient, the object height, and the coordinates of the object frame.

4 Claims, 16 Drawing Sheets

(56) References Cited

OTHER PUBLICATIONS

Kaiming He et al., Mask R-CNN, Proceedings of the IEEE International Conference on Computer Vision (ICCV), 2017, Oct. 22, 2017, pp. 2961-2969.
Masako Kashiwagi et al., Deep Depth From Aberration Map, ICCV 2019, Oct. 27, 2019, pp. 4070-4079.

* cited by examiner

Fig. 4

|  | P1 SECTION | P2 SECTION | P3 SECTION | P4 SECTION |
|---|---|---|---|---|
| FEATURE POINT K1 | ● | ● | ● | ● |
| FEATURE POINT K2 |  |  |  | ● |
| FEATURE POINT K3 |  |  | ● | – |
| FEATURE POINT K4 |  | ● | – | – |
| FEATURE POINT K5 | ● | – | – | – |

Fig. 5

| MISSING PATTERN IN P1 SECTION | DISTANCE ADDITION PATTERN | CORRECTION COEFFICIENT |
|---|---|---|
| P1A (MISSING: K2) | K1-K3, K3-K4, K4-K5 | HP1A |
| P1B (MISSING: K2, K3) | K1-K4, K4-K5 | HP1B |
| P1C (MISSING: K2, K3, K4) | K1-K5 | HP1C |
| P1D (MISSING: K2, K4) | K1-K3, K3-K5 | HP1D |
| P1E (MISSING: K3) | K1-K2, K2-K4, K4-K5 | HP1E |
| P1F (MISSING: K3, K4) | K1-K2, K2-K5 | HP1F |
| P1G (MISSING: K4) | K1-K2, K2-K3, K3-K5 | HP1G |
| P1H (NO MISSING IN P1 SECTION) | K1-K2, K2-K3, K3-K4, K4-K5 | HP1H |
| MISSING PATTERN IN P2 SECTION | DISTANCE ADDITION TARGET | CORRECTION COEFFICIENT |
| P2A (MISSING: K2) | K1-K3, K3-K4 | HP2A |
| P2B (MISSING: K2, K3) | K1-K4 | HP2B |
| P2C (MISSING: K3) | K1-K2, K2-K4 | HP2C |
| P2D (NO MISSING IN P2 SECTION) | K1-K2, K2-K3, K3-K4 | HP2D |
| MISSING PATTERN IN P3 SECTION | DISTANCE ADDITION TARGET | CORRECTION COEFFICIENT |
| P3A (MISSING: K2) | K1-K3 | HP3A |
| P3B (NO MISSING IN P3 SECTION) | K1-K2, K2-K3 | HP3B |
| MISSING PATTERN IN P4 SECTION | DISTANCE ADDITION TARGET | CORRECTION COEFFICIENT |
| P4A (NO MISSING IN P4 SECTION) | K1-K2 | HP4A |

Fig. 6

|  | T1 SECTION | T2 SECTION | T3 SECTION | T4 SECTION | T5 SECTION | T6 SECTION |
|---|---|---|---|---|---|---|
| FEATURE POINT K1 | – | – | – | – | – | – |
| FEATURE POINT K2 | ● | ● | ● | – | – | – |
| FEATURE POINT K3 |  |  | ● | ● | – | ● |
| FEATURE POINT K4 |  | ● | – |  | ● | ● |
| FEATURE POINT K5 | ● | – | – | ● | ● | – |

Fig. 7

| MISSING PATTERN IN T1 SECTION | DISTANCE ADDITION PATTERN | CORRECTION COEFFICIENT |
|---|---|---|
| T1A (MISSING: K3) | K2-K4, K4-K5 | HT1A |
| T1B (MISSING: K3, K4) | K2-K5 | HT1B |
| T1C (MISSING: K4) | K2-K3, K3-K5 | HT1C |
| T1D (NO MISSING IN T1 SECTION) | K2-K3, K3-K4, K4-K5 | HT1D |
| MISSING PATTERN IN T2 SECTION | DISTANCE ADDITION TARGET | CORRECTION COEFFICIENT |
| T2A (MISSING: K3) | K2-K4 | HT2A |
| T2B (NO MISSING IN T2 SECTION) | K2-K3, K3-K4 | HT2B |
| MISSING PATTERN IN T3 SECTION | DISTANCE ADDITION TARGET | CORRECTION COEFFICIENT |
| T3A (MISSING: K2, K3) | K2-K3 | HT3A |
| MISSING PATTERN IN T4 SECTION | DISTANCE ADDITION TARGET | CORRECTION COEFFICIENT |
| T4A (MISSING: K4) | K3-K5 | HT4A |
| T4B (NO MISSING IN T2 SECTION) | K3-K4, K4-K5 | HT4B |
| MISSING PATTERN IN T5 SECTION | DISTANCE ADDITION TARGET | CORRECTION COEFFICIENT |
| T5A (NO MISSING IN T5 SECTION) | K4-K5 | HT5A |
| MISSING PATTERN IN T6 SECTION | DISTANCE ADDITION TARGET | CORRECTION COEFFICIENT |
| T6A (NO MISSING IN T6 SECTION) | K3-K4 | HT6A |

Fig. 8

| SUBJECT IDENTIFICATION DATA | SUBJECT FRAME HEIGHT (CORRECT HEIGHT) (PIXELS) | MISSING PATTERN P1A DISTANCE ADDITION RESULT (PIXELS) | MISSING PATTERN P1A CORRECTION COEFFICIENT HP1A | MISSING PATTERN P1B DISTANCE ADDITION RESULT (PIXELS) | MISSING PATTERN P1B CORRECTION COEFFICIENT HP1B | ... | MISSING PATTERN T6A DISTANCE ADDITION RESULT (PIXELS) | MISSING PATTERN T6A CORRECTION COEFFICIENT HT6A | APPLICABILITY |
|---|---|---|---|---|---|---|---|---|---|
| 1 | S1 | P1A_1 | S1/P1A_1 | P1B_1 | S1/P1B_1 | ... | T6A_1 | S1/T6A_1 | APPLICABLE |
| ... | ... | ... | ABNORMAL VALUE (CORRECTION COEFFICIENT LARGER THAN FIRST THRESHOLD) | ... | ... | ... | ... | ... | NOT APPLICABLE |
| ... | ... | ... | ... | ... | ABNORMAL VALUE (CORRECTION COEFFICIENT SMALLER THAN SECOND THRESHOLD) | ... | ... | ... | NOT APPLICABLE |
| N | SN | P1A_N | SN/P1A_N | P1B_N | SN/P1B_N | ... | T6A_N | SN/T6A_N | APPLICABLE |
|  | AVERAGE VALUE OF SUBJECT FRAME HEIGHT | AVERAGE VALUE OF MISSING PATTERN P1A DISTANCE ADDITION RESULT | AVERAGE VALUE AVE_HP1A OF MISSING PATTERN P1A CORRECTION COEFFICIENT HP1A | AVERAGE VALUE OF MISSING PATTERN P1B DISTANCE ADDITION RESULT | AVERAGE VALUE AVE_HP1B OF MISSING PATTERN P1A CORRECTION COEFFICIENT HP1A | ... | AVERAGE VALUE OF MISSING PATTERN T6A DISTANCE ADDITION RESULT | AVERAGE VALUE AVE_HT6A OF MISSING PATTERN T6A CORRECTION COEFFICIENT HT6A | |

Fig. 9

| OBJECT NAME | OBJECT HEIGHT (CORRECT HEIGHT) (cm) |
|---|---|
| TABLE_A | 70 |
| CHAIR_A | 80 |
| SOFA_A | 70 |
| BICYCLE_A | 90 |
| PASSENGER CAR_A | 145 |
| BAG_A | 30 |
| BAG_B | 40 |
| BOOK_A | 25 |
| ... | ... |

HEIGHT ESTIMATION METHOD, HEIGHT ESTIMATION APPARATUS, AND PROGRAM

CROSS-REFERENCE TO RELATED APPLICATIONS

This application is a 371 U.S. National Phase of International Application No. PCT/JP2020/006749, filed on Feb. 20, 2020. The entire disclosure of the above application is incorporated herein by reference.

TECHNICAL FIELD

The present invention relates to a height estimation method, a height estimation apparatus, and a program.

BACKGROUND ART

A height of a person captured in an image is estimated sometimes. NPL 1 discloses a method of extracting each feature point predetermined along a skeleton of a person captured in an image from the image. NPL 2 discloses a method of deriving a frame surrounding a person or object captured in an image on the image. These methods are sometimes used to estimate a height of a person captured in an image.

NPL 3 discloses a method of estimating depth in a single image. The method disclosed in NPL 3 estimates depth of a position of a person on the basis of distortion of an edge of the person captured in the image. The method disclosed in NPL 3 allows for estimating depth of a person and an object captured in an image.

CITATION LIST

Non Patent Literature

NPL 1: Zhe Cao, Tomas Simon, Shih-En Wei, Yaser Sheikh, "Realtime Multi-Person 2D Pose Estimation using Part Affinity Fields", CVPR, 2017.
NPL 2: Kaiming He, Georgia Gkioxari, Piotr Dollar, Ross Girshick, "Mask R-CNN", The IEEE International Conference on Computer Vision (ICCV), 2017, pp. 2961-2969.
NPL 3: Masako Kashiwagi, Nao Mishima, Tatsuo Kozakaya, Shinsaku Hiura, "Deep Depth From Aberration Map", ICCV 2019, pp 4070-4079.

SUMMARY OF THE INVENTION

Technical Problem

FIG. 16 is a diagram illustrating an example of estimated height. A subject image 200 is an image of a subject (person). An object image 400 is an image of an object (for example, a bag or book). The subject (person) and the object are in a positional relationship with no depth difference from a camera. A feature point 201 is a feature point of the head (face) of the subject. A feature point 202 is a feature point under the neck of the subject. A feature point 203 is a feature point of the waist of the subject. A feature point 204 is a feature point of the right knee of the subject. A feature point 205 is a feature point of the left knee of the subject. A feature point 206 is a feature point of the right foot of the subject. A feature point 207 is a feature point of the left foot of the subject.

In the upper left image of FIG. 16, the entire body of the subject is captured. When the entire body of the subject is captured in the image as described above, the height of the subject can be estimated on the basis of a summing result of the distance between the feature points extracted from the image.

However, the entire body of the subject is not necessarily captured in the image. In the upper right image of FIG. 16, the feature point 206 and the feature point 207 of the subject are not extracted from the image. In the lower left image of FIG. 16, the feature point 202 and the feature point 203 are not extracted from the image because the feature points are shielded by an object 404. The feature point 206 and the feature point 207 are not extracted from the image because the feature points are shielded by an obstacle 405. In the lower right image of FIG. 16, the feature point 201, the feature point 204, and the feature point 205 are not extracted from the image.

As described above, to improve the accuracy of estimating the height of a subject on the basis of an image, all of the feature points predetermined along the skeleton of the subject need to be extracted from the image.

In view of the above circumstances, an object of the present invention is to provide a height estimation method, a height estimation apparatus, and a program capable of improving accuracy of estimating the height of a subject on the basis of an image even when some of feature points predetermined along a skeleton of the subject are not extracted from the image.

Means for Solving the Problem

One aspect of the present invention is a height estimation method performed by a height estimation apparatus, and the method includes a first feature point extraction step of extracting, from a first input image in which a subject image that is an image of a subject is captured, a feature point coordinate that is a coordinate of a feature point predetermined along a skeleton of the subject image, a first coordinate estimation step of estimating a coordinate of a first subject frame that is a frame surrounding the subject image in the first input image, a pre-generation step of deriving a height of the first subject frame in the first input image on the basis of the coordinate of the first subject frame and generating a distance addition pattern that is an addition pattern of a distance between a feature point coordinate and another feature point coordinate and a correction coefficient for each missing pattern that is a pattern of a combination of one or a plurality of the feature point coordinates that are not extracted among the plurality of the feature point coordinates predetermined, a second feature point extraction step of extracting a feature point coordinate from a second input image in which an object image that is an image of an object and the subject image are captured, a second coordinate estimation step of estimating a coordinate of a second subject frame that is a frame surrounding the subject image in the second input image and estimating a coordinate of an object frame that is a frame surrounding the object image in the second input image, a subject data selection step of selecting the missing pattern and the correction coefficient on the basis of the feature point coordinate extracted from the second input image, an object data selection step of selecting an object height that is a height of the object in the object image in the second input image on the basis of information on the object image in the second input image, and a height estimation step of adding up a distance between a feature point coordinate and another feature point coordinate extracted from the second input image on the basis of the missing pattern selected and deriving an estimated value of the height of the subject on the basis of a result of adding up the distance between the feature point coordinate and the other feature point coordinate in the second input image, the correction coefficient selected, the object height, and the coordinate of the object frame.

One aspect of the present invention is a height estimation apparatus including a first feature point extraction unit that extracts, from a first input image in which a subject image that is an image of a subject is captured, a feature point coordinate that is a coordinate of a feature point predetermined along a skeleton of the subject image, a first coordinate estimation unit that estimates coordinates of a first subject frame that is a frame surrounding the subject image in the first input image, a pre-generation unit that derives a height of the first subject frame in the first input image on the basis of the coordinate of the first subject frame and generates a distance addition pattern that is an addition pattern of a distance between a feature point coordinate and another feature point coordinate and a correction coefficient for each missing pattern that is a pattern of a combination of one or a plurality of the feature point coordinates that are not extracted among the plurality of the feature point coordinates predetermined, a second feature point extraction unit that extracts a feature point coordinate from a second input image in which an object image that is an image of an object and the subject image are captured, a second coordinate estimation unit that estimates a coordinate of a second subject frame that is a frame surrounding the subject image in the second input image and estimates a coordinate of an object frame that is a frame surrounding the object image in the second input image, a subject data selection unit that selects the missing pattern and the correction coefficient on the basis of the feature point coordinate extracted from the second input image, an object data selection unit that selects an object height that is a height of the object in the object image in the second input image in accordance with information on the object image in the second input image, and a height estimation unit that adds up a distance between a feature point coordinate and another feature point coordinate extracted from the second input image in accordance with the missing pattern selected and derives an estimated value of the height of the subject in accordance with a result of adding up the distance between the feature point coordinate and the other feature point coordinate in the second input image, the correction coefficient selected, the object height, and the coordinate of the object frame.

One aspect of the present invention is a program for causing a computer to function as the height estimation apparatus described above.

Effects of the Invention

According to the present invention, it is possible to provide a height estimation method, a height estimation apparatus, and a program capable of improving accuracy of estimating the height of a subject on the basis of an image even in a case where some of predetermined feature points along a skeleton of the subject is not extracted from the image.

BRIEF DESCRIPTION OF DRAWINGS

FIG. 4 illustrates a first example of a missing pattern for each section of a feature point in the embodiment.

FIG. 5 is a diagram illustrating a first example of association among a missing pattern, a distance addition target, and a correction coefficient in the embodiment.

FIG. 6 illustrates a second example of a missing pattern for each section of a feature point in the embodiment.

FIG. 7 is a diagram illustrating a second example of association between a missing pattern, a distance addition target, and a correction coefficient in the embodiment.

FIG. 8 is a diagram illustrating an example of a data table of missing data including a missing pattern according to the embodiment.

FIG. 9 is a diagram illustrating an example of association between an object name and an object height in the embodiment.

DESCRIPTION OF EMBODIMENTS

Embodiments of the present invention will be described in detail with reference to the drawings.

Figure 1:
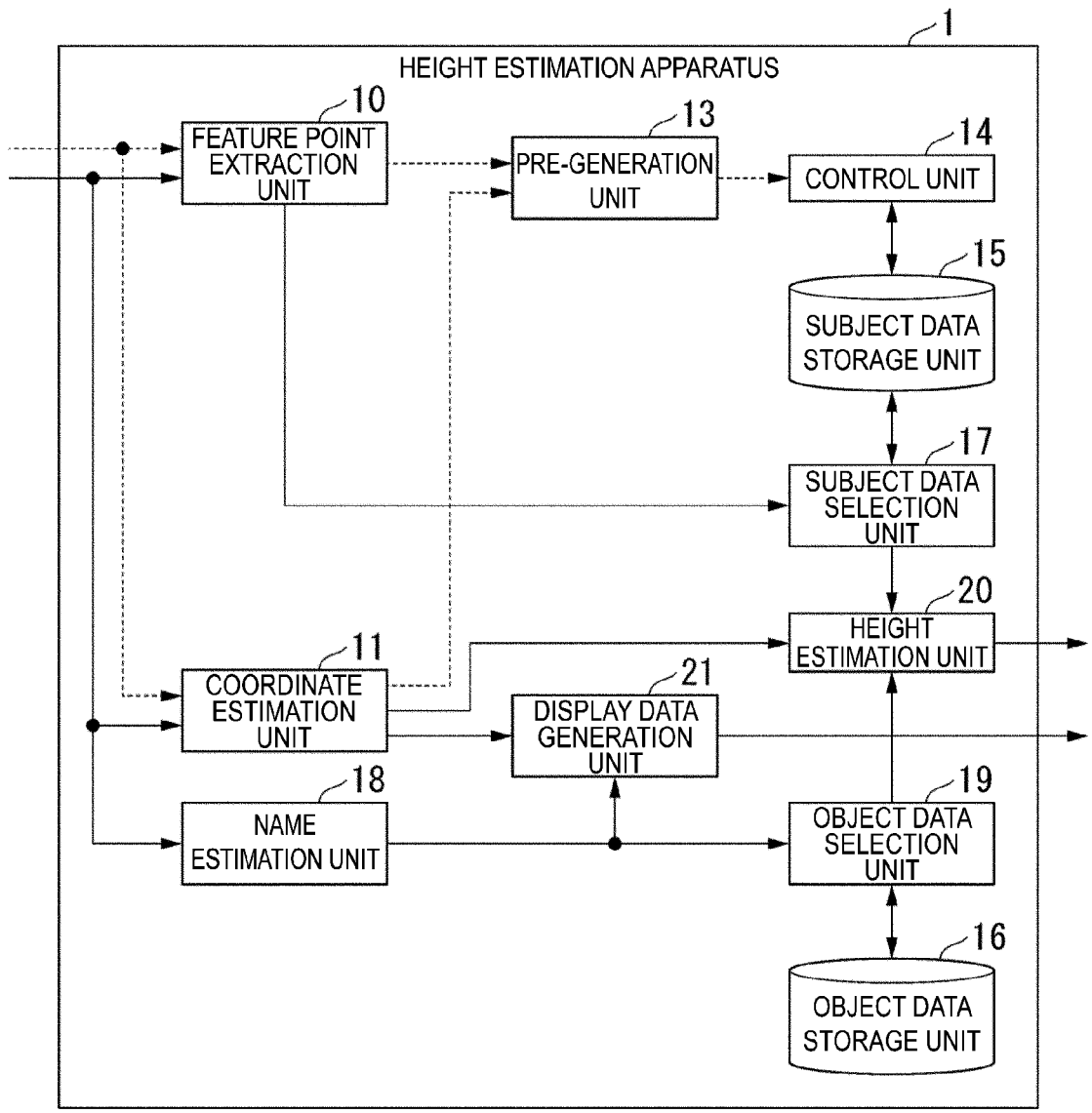
FIG. 1 is a diagram illustrating a configuration example of a height estimation apparatus in an embodiment.

FIG. 1 is a diagram illustrating a configuration example of a height estimation apparatus 1. The height estimation apparatus 1 is an apparatus that estimates a height of a subject captured in an image on the basis of the image. The subject is, for example, a person, a humanoid robot, or a doll. In the following, the subject is a person as an example.

The height estimation apparatus 1 includes a feature point extraction unit 10, a coordinate estimation unit 11, a pre-generation unit 13, a control unit 14, a subject data storage unit 15, an object data storage unit 16, a subject data selection unit 17, a name estimation unit 18, an object data selection unit 19, a height estimation unit 20, and a display data generation unit 21.

Figure 2:
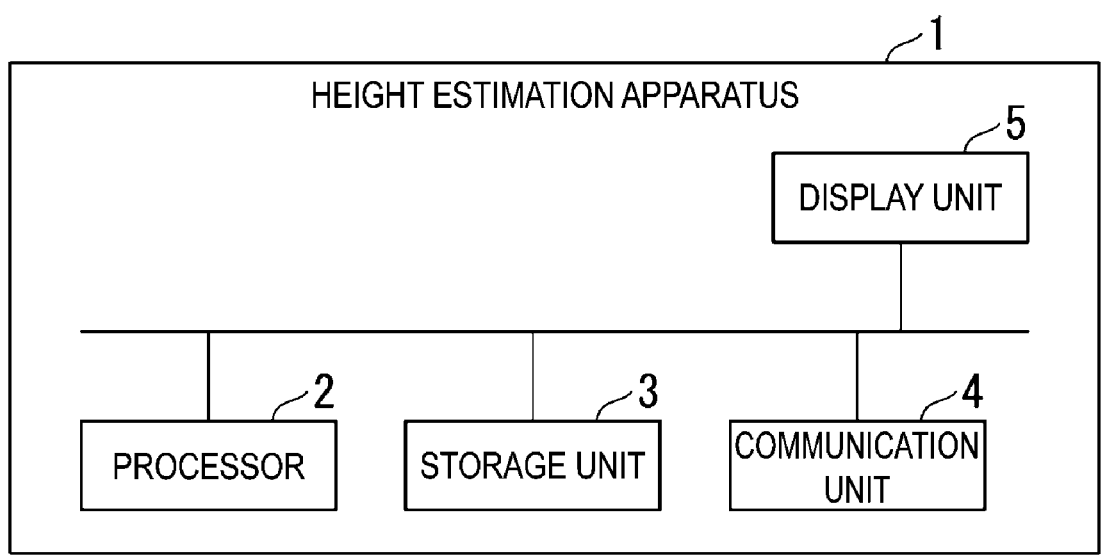
FIG. 2 is a diagram illustrating an example of a hardware configuration of the height estimation apparatus in the embodiment.

FIG. 2 is a diagram illustrating an example of a hardware configuration of the height estimation apparatus 1. The height estimation apparatus 1 includes a processor 2, a storage unit 3, a communication unit 4, and a display unit 5.

Some or all of the feature point extraction unit 10, the coordinate estimation unit 11, the pre-generation unit 13, the control unit 14, the subject data selection unit 17, the name estimation unit 18, the object data selection unit 19, the height estimation unit 20, and the display data generation unit 21 are implemented in software by the processor 2 such as a central processing unit (CPU) executing a program stored in the storage unit 3 having a non-volatile recording medium (non-temporary recording medium). The program may be recorded on a computer-readable recording medium. The computer-readable recording medium is a portable medium such as a flexible disk, a magneto-optical disc, a read only memory (ROM), or a CD-ROM or a non-temporary recording medium such as a storage device such as a hard disk provided in a computer system. The communication unit 4 may receive the program via a communication line. The communication unit 4 may transmit a classification result of an action via a communication line. The display unit 5 displays an image. The display unit 5 is, for example, a liquid crystal display.

Some or all of the feature point extraction unit 10, the coordinate estimation unit 11, the pre-generation unit 13, the control unit 14, the subject data selection unit 17, the name estimation unit 18, the object data selection unit 19, the height estimation unit 20, and the display data generation unit 21 may be implemented by using, for example, hardware including an electronic circuit (or circuitry) using a large scale integration circuit (LSI), an application specific integrated circuit (ASIC), a programmable logic device (PLD), a field programmable gate array (FPGA), or the like.

Figure 3:
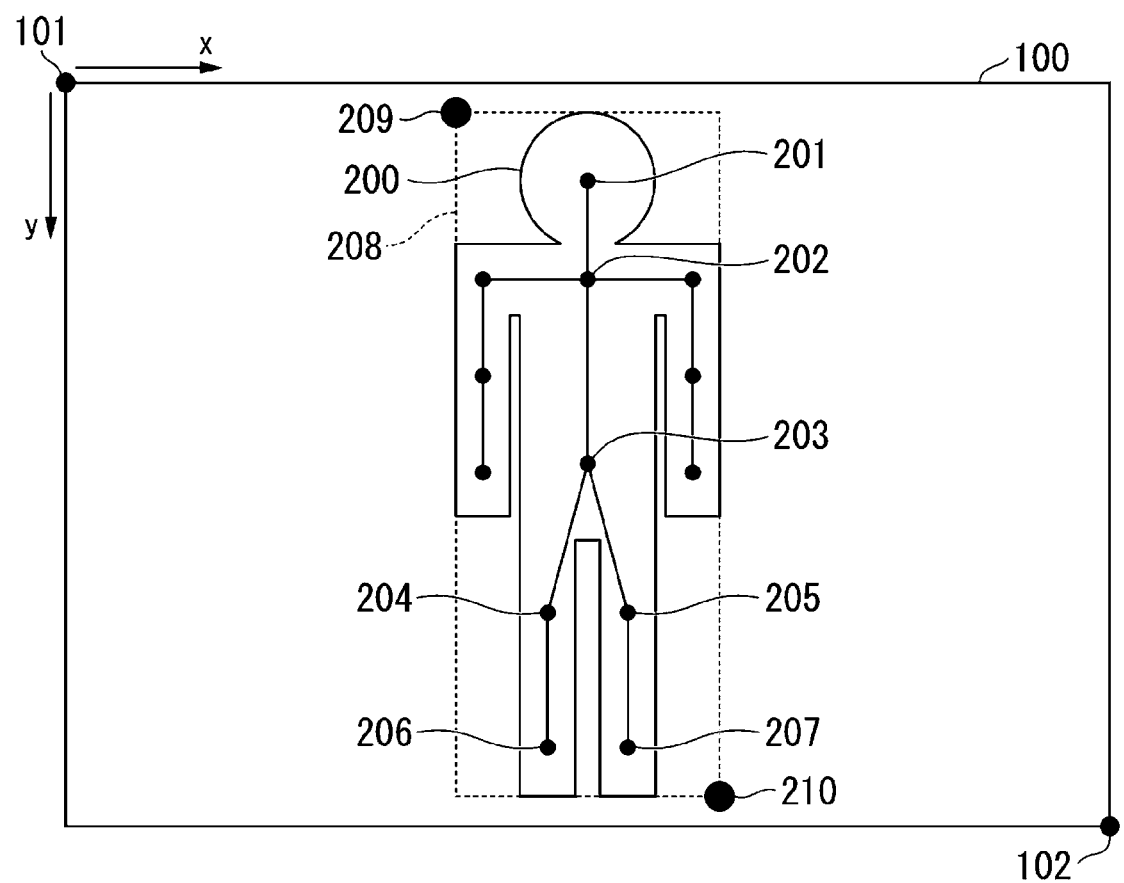
FIG. 3 is a diagram illustrating a first example of feature points extracted from an input image and estimated feature point coordinates in the embodiment.

Next, pre-processing at a stage prior to estimation processing will be described. FIG. 3 is a diagram illustrating a first example of feature points extracted from an input image 100 (first input image) and estimated feature point coordinates. The feature point extraction unit 10 (first feature point extraction unit) acquires the input image 100 from an external device (not illustrated). In the input image 100, a subject image 200 of the entire body of the subject facing the front is captured. An object other than the subject may not be captured in the input image 100. The input image 100 may be associated with identification data "n" (n is any integer from 1 to N)" for identifying a person.

Each feature point from a feature point 201 to a feature point 207 is predetermined along the skeleton of the subject image 200 (entire body) of the input image 100. A feature point 201 is a feature point of the head (face) of the subject. A feature point 202 is a feature point under the neck of the subject. A feature point 203 is a feature point of the waist of the subject. A feature point 204 is a feature point of the right knee of the subject. A feature point 205 is a feature point of the left knee of the subject. A feature point 206 is a feature point of the right foot of the subject. A feature point 207 is a feature point of the left foot of the subject.

The feature point extraction unit 10 outputs, to the pre-generation unit 13, coordinates of each feature point from the feature point 201 to the feature point 207 predetermined along the skeleton of the subject image 200 (entire body) of the input image 100. The feature point extraction unit 10 may output, to the pre-generation unit 13, an input image maximum point 102, which is a point at which the coordinates are the maximum value in the input image 100, as a size of the input image 100, with an input image origin 101, which is an origin of the xy coordinates of the input image, as an origin.

The coordinate estimation unit 11 (first coordinate estimation unit) estimates coordinates of a subject frame 208 (first subject frame) that is a frame surrounding the subject image 200 in the input image 100. A subject frame origin 209 illustrated in FIG. 3 is coordinates (minimum coordinates) of the upper left corner of the subject frame 208 in the input image 100. A subject frame maximum point 210 is coordinates (maximum coordinates) of the lower right corner of the subject frame 208 in the input image 100. The coordinate estimation unit 11 outputs the coordinates of the subject frame 208 to the pre-generation unit 13.

The pre-generation unit 13 outputs, from the feature point extraction unit 10, coordinates of each feature point from the feature point 201 to the feature point 207 predetermined along the skeleton of the subject image 200 (entire body) of the input image 100. The pre-generation unit 13 acquires the coordinates of the subject frame 208 from the coordinate estimation unit 11.

The pre-generation unit 13 generates a missing pattern that is a pattern of a combination of one or more feature point coordinates not extracted among the feature points from the feature points 201 to the feature points 207.

FIG. 4 is a diagram illustrating a first example of a missing pattern for each section of a feature point. FIG. 4 illustrates an example of a missing pattern for each section of a feature point when the feature point 201 is extracted from the image.

A feature point "K1" is the feature point 201 of the head (face) of the subject. A feature point "K2" is the feature point 202 under the neck of the subject. A feature point "K3" is the feature point 203 of the waist of the subject. A feature point "K4" is a midpoint between the feature point 204 of the right knee of the subject and the feature point 205 of the left knee of the subject. A feature point "K5" is a midpoint between the feature point 206 of the right foot of the subject and the feature point 207 of the left foot of the subject.

A "P1 section" is a section from the feature point "K1" to the feature point "K5". In the "P1 section", one or more of the feature points from the feature point "K2" to the feature point "K4" may be missing without being extracted.

A "P2 section" is a section from the feature point "K1" to the feature point "K4". In the "P2 section", one or more of the feature point "K2" or the feature point "K3" may be missing without being extracted.

A "P3 section" is a section from the feature point "K1" to the feature point "K3". In the "P3 section", the feature point "K2" may be missing without being extracted. A "P4 section" is a section from the feature point "K1" to the feature point "K2".

The pre-generation unit 13 generates, for each generated missing pattern, a distance addition pattern, which is an addition pattern of the distance between the height of the subject frame 208 and the feature point coordinates, and a correction coefficient. The pre-generation unit 13 outputs, for each piece of subject identification data "n", a subject frame height (correct height), which is a height of a frame surrounding the subject in the image, and a combination of the missing pattern, the distance addition result, and the correction coefficient to the control unit 14. Details of the pre-generation unit 13 will be described later using FIG. 12.

FIG. 5 is a diagram illustrating a first example of association among a missing pattern, a distance addition target, and a correction coefficient. In the data table illustrated in FIG. 5, for example, the missing pattern in the P1 section, the distance addition pattern, and the correction coefficient are associated. The data table illustrated in FIG. 5 is recorded in the subject data storage unit 15 by the pre-generation unit 13 or the control unit 14.

FIG. 6 is a diagram illustrating a second example of a missing pattern for each section of a feature point. FIG. 6 illustrates an example of a missing pattern for each section of a feature point for a case in which the feature point 201 (feature point "K1") is not extracted from the image.

A "T1 section" is a section from the feature point "K2" to the feature point "K5". In the "T1 section", one or more of the feature points from the feature point "K3" to the feature point "K4" may be missing without being extracted. A "T2 section" is a section from the feature point "K2" to the feature point "K4". In the "T2 section", the feature point "K3" may be missing without being extracted. A "T3 section" is a section from the feature point "K2" to the feature point "K3".

A "T4 section" is a section from the feature point "K3" to the feature point "K5". In the "T4 section", the feature point "K4" may be missing without being extracted. A "T5 section" is a section from the feature point "K4" to the feature point "K5". A "T6 section" is a section from the feature point "K3" to the feature point "K4".

FIG. 7 is a diagram illustrating a second example of association among the missing pattern, the distance addition target, and the correction coefficient. In the data table illustrated in FIG. 7, for example, the missing pattern in the T1 section, the distance addition pattern, and the correction coefficient are associated. The data table illustrated in FIG. 7 is recorded in the subject data storage unit 15 by the pre-generation unit 13 or the control unit 14.

As described above, for a case where one or more of the feature points from the feature point 201 to the feature point 207 are not extracted, association among the missing pattern, the distance addition pattern, and the correction coefficient is derived.

FIG. 8 is a diagram illustrating an example of a data table of missing data including a missing pattern. In the data table illustrated in FIG. 8, for each piece of subject identification data "n", the subject frame height (correct height), the distance addition result of each missing pattern, the correction coefficient in each missing pattern, and applicability of the correction coefficient are associated with each other.

The control unit 14 determines applicability of the correction coefficient on the basis of whether a correction coefficient is included in a range between a predetermined first threshold and a second threshold smaller than the first threshold for the data table of missing data. The control unit 14 detects, of elements of the missing data, an element outside of the range between the first threshold and the second threshold as an abnormal value (an outlier value). This range is determined on the basis of an average value of missing data (for example, correction coefficient) in the plurality of pieces of subject identification data. The control unit 14 updates the applicability in accordance with the detection result of the abnormal value. The correction coefficient determined to be not applicable is not used.

The subject data storage unit 15 stores a data table in which the missing pattern, the distance addition pattern, and the correction coefficient are associated. The subject data storage unit 15 stores, for each piece of subject identification data "n", a data table in which the subject frame height (correct height) of the subject frame 208 and a combination of the missing pattern, the distance addition result, and the correction coefficient are associated with each other. The subject data storage unit 15 stores a height of the subject frame 208 in the input image 100.

The object data storage unit 16 pre-stores a data table associated with the object name and the object height (correct height).

FIG. 9 is a diagram illustrating an example of association among an object name and an object height (correct height). Hereinafter, the height of an object imaged with the subject is known. In FIG. 9, an object name and an object height are associated with each other. For example, the object name "table_A" of the table is associated with the height of the table "70 cm". The data table illustrated in FIG. 9 is stored in advance in the object data storage unit 16.

Next, estimation processing will be described.

Figure 10:
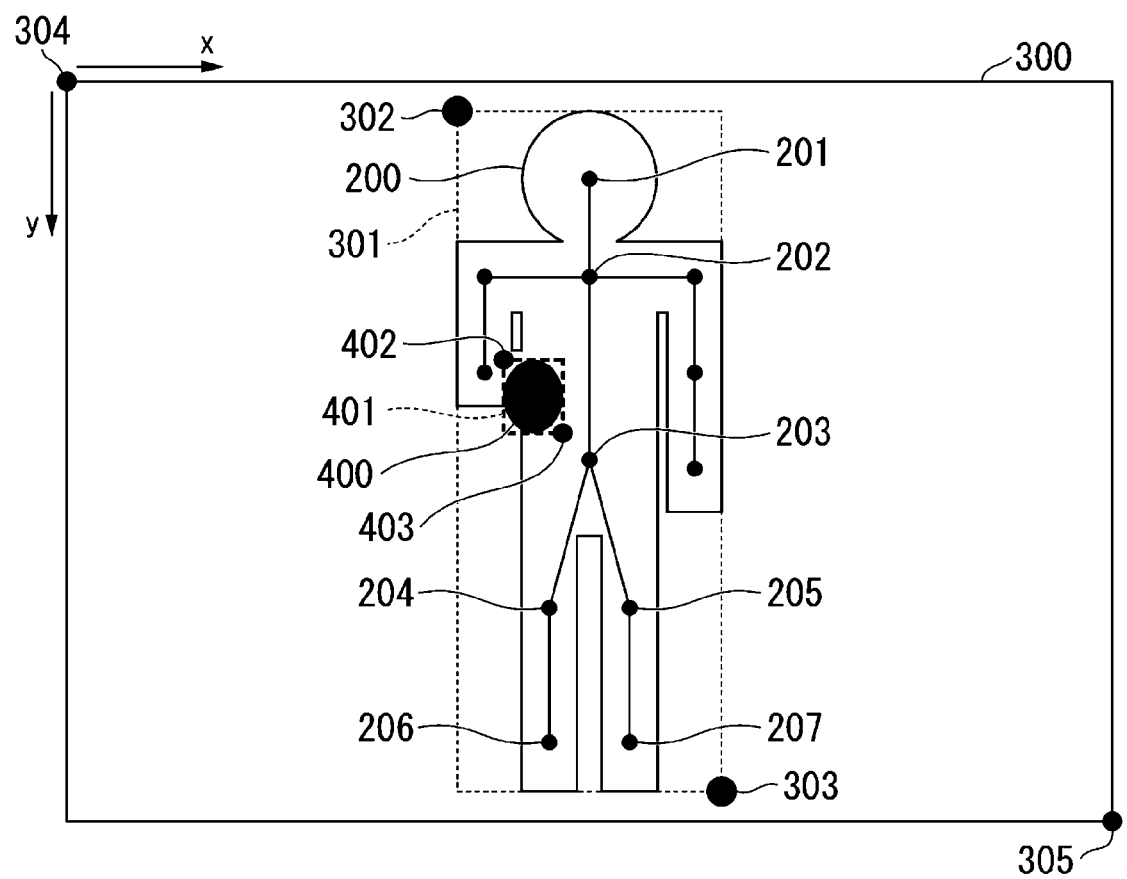
FIG. 10 is a diagram illustrating a second example of feature points extracted from an input image and estimated feature point coordinates in the embodiment.

FIG. 10 is a diagram illustrating a second example of feature points extracted from an input image 300 (second input image) and estimated feature point coordinates. In FIG. 10, the subject (person) whose height is estimated and an object are captured in the input image 300 (frame). The subject (person) and the object are in a positional relationship with no depth difference from a camera.

The feature point extraction unit 10 (second feature point extraction unit) acquires the input image 300 in which the object image 400 and the subject image 200 are captured. In the input image 300, the subject facing forward, sideways, or backward is captured. A portion of the subject may not be captured in the input image 300.

The feature point extraction unit 10 extracts, from the input image 300, coordinates of at least one of the feature points from the feature point 201 to the feature point 207 predetermined along a skeleton of the subject image 200 of the input image 300. The feature point extraction unit 10 outputs each extracted feature point coordinates to the subject data selection unit 17.

The coordinate estimation unit 11 (second coordinate estimation unit) estimates coordinates of a subject frame 301 (second subject frame) that is a frame surrounding the subject image 200 in the input image 300. The subject frame origin 302 is coordinates (minimum coordinates) of the upper left corner of the subject frame 301. The subject frame maximum point 303 is coordinates (maximum coordinates) of the lower right corner of the subject frame 301. The coordinate estimation unit 11 outputs the coordinates of the subject frame 301 to the display data generation unit 21.

The coordinate estimation unit 11 estimates coordinates of an object frame 401, which is a frame surrounding the object image 400 in the input image 300. The object frame origin 402 is coordinates (minimum coordinates) of the upper left corner of the object frame 401. The object frame maximum point 403 is coordinates (maximum coordinates) of the lower right corner of the object frame 401. The coordinate estimation unit 11 outputs the coordinates of the object frame 401 to the height estimation unit 20 and the display data generation unit 21.

The subject data selection unit 17 (subject data collation unit) acquires the coordinates of each feature point extracted from the input image 300 from the feature point extraction unit 10. The subject data selection unit 17 selects, on the basis of each feature point coordinate extracted from the input image 300, a missing pattern of each feature point and a correction coefficient that is a coefficient for correcting an estimated value of a height of the subject from the data table stored in the subject data selection unit 17. The subject data selection unit 17 outputs, to the height estimation unit 20, the missing pattern of the feature point coordinates in the input image 300, and the feature point coordinates and the correction coefficient selected on the basis of the missing pattern.

The name estimation unit 18 acquires the input image 300 from an external device (not illustrated). The name estimation unit 18 estimates a name of the object captured in the input image 300. The name estimation unit 18 outputs a name of the object of the object image 400 in the input image 300 to the object data selection unit 19 and the display data generation unit 21.

The object data selection unit 19 (object data collation unit) acquires the name of the object of the object image 400 in the input image 300 from the name estimation unit 18. The object data selection unit 19 selects the object height associated with the name of the object of the object image 400 in the input image 300 from the data table stored in the object data storage unit 16. The object data selection unit 19 outputs the object height associated with the name of the object of the object image 400 in the input image 300 to the height estimation unit 20.

The height estimation unit 20 acquires, from the subject data selection unit 17, a missing pattern of feature point coordinates in the input image 300, and the feature point coordinates and the correction coefficient selected on the basis of the missing pattern. The height estimation unit 20 acquires coordinates of the object frame 401 from the coordinate estimation unit 11. The height estimation unit 20 acquires, from the object data selection unit 19, an object height associated with a name of an object of the object image 400 in the input image 300.

The height estimation unit 20 derives a height (object frame height) of the object frame 401 on the basis of coordinates (object frame coordinates) of the object frame 401. The height estimation unit 20 selects an addition pattern (distance addition pattern) of the distance between the feature point coordinates of the input image 300, on the basis of the missing pattern of the feature point coordinates in the input image 300. The height estimation unit 20 derives a result of adding the distance between the feature point coordinates (distance addition result) on the basis of the distance addition pattern. The height estimation unit 20 estimates the height of the subject of the subject image 200, as in Equation (1), on the basis of the object height, the distance addition result, the correction coefficient, and the object frame height.

$$\text{Estimated value of height of subject} = \text{distance addition result} \times \text{correction coefficient} \times \text{object height} / \text{object frame height} \quad (1)$$

The unit of "estimated value of height of subject" is, for example, centimeters. The correction coefficient is expressed as Equation (2).

$$\text{Correction coefficient} = (\text{height of subject frame in } y\text{-axis}) / \text{distance addition result} \quad (2)$$

The unit of height in the y-axis direction of the subject frame is, for example, pixels. The unit of "object height" is, for example, centimeters. The unit of "distance addition result" is, for example, pixels. The unit of "object frame height" is, for example, pixels. The "object frame height" is expressed as Equation (3).

$$\text{Object frame height} = |(y \text{ coordinate of object frame maximum point}) - (y \text{ coordinate of object frame origin})| \quad (3)$$

For example, in FIG. 10, the height (object frame height) of the object frame 401 is an absolute value of a difference between the y coordinate of the object frame maximum point 403 and the y coordinate of the object frame origin 402. Details of the height estimation unit 20 are described later with reference to FIG. 14.

The display data generation unit 21 acquires, from the coordinate estimation unit 11, the subject frame origin 302 and the subject frame maximum point 303 in the input image 300 as coordinates of the subject frame 301. The display data generation unit 21 acquires, from the coordinate estimation unit 11, the object frame origin 402 and the object frame maximum point 403 in the input image 300 as coordinates of the object frame 401. The display data generation unit 21 acquires the name of the object of the object image 400 in the input image 300 from the name estimation unit 18.

Figure 11:
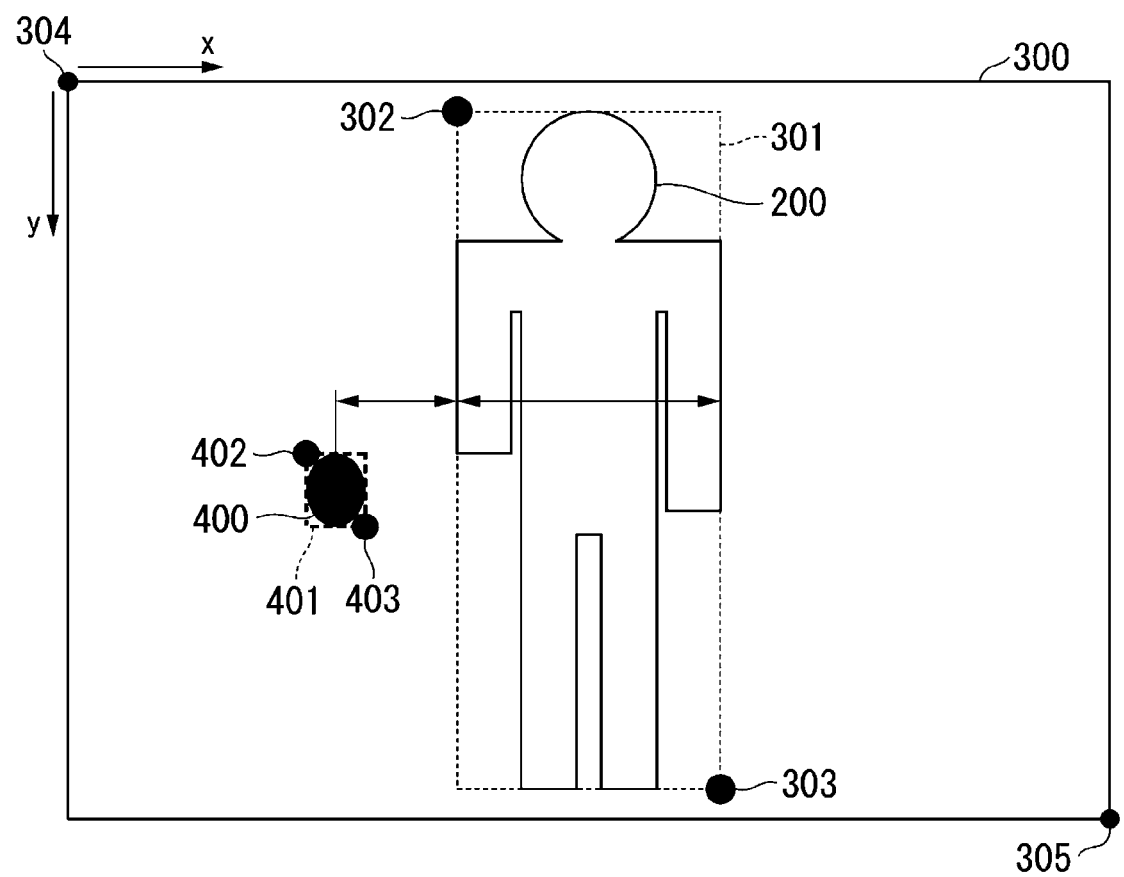
FIG. 11 is a diagram illustrating an example of a positional relationship between a subject and an object in the embodiment.

FIG. 11 is a diagram illustrating an example of a positional relationship between the subject and the object. The shorter the distance between the subject image 200 and the object image 400 in the input image 300, the higher the reliability of the estimated value of the height of the subject (person). Thus, the display data generation unit 21 causes the display unit 5 to display information on the distance between the subject image 200 and the object image 400. For example, the display data generation unit 21 may cause the display unit 5 to display that the object frame 401 is present in a one-half body width distance in the x-axis direction from the subject frame 301. The display data generation unit 21 may cause the display unit 5 to display the name of the object of the object image 400. Details of the display data generation unit 21 are described later with reference to FIG. 15.

Figure 12:
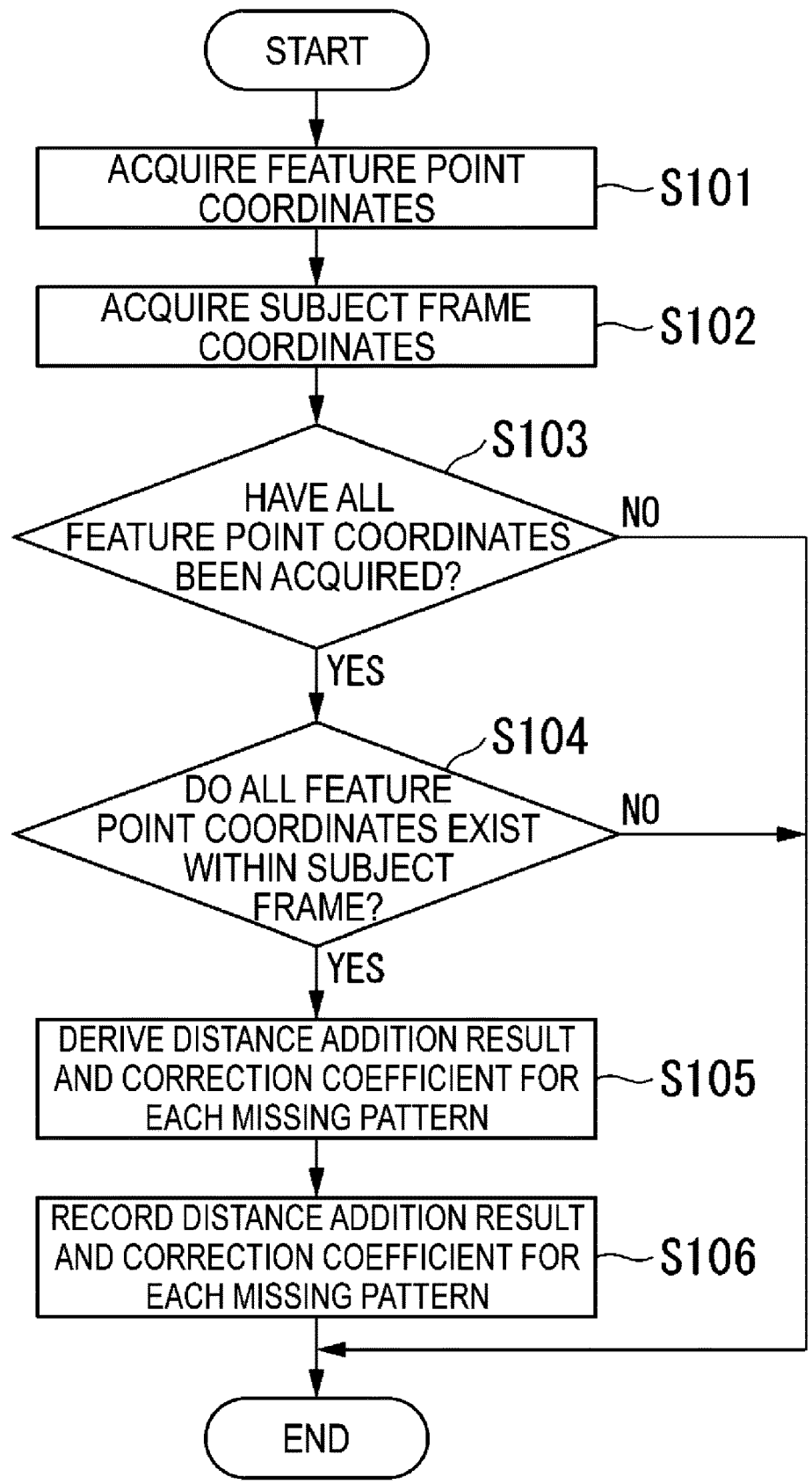
FIG. 12 is a flowchart illustrating an operation example of a pre-generation unit in the embodiment.

Next, an operation example of the height estimation apparatus 1 will be described. FIG. 12 is a flowchart illustrating an operation example of the pre-generation unit 13. The operations illustrated in FIG. 12 are performed at a stage prior to the stage of the estimation processing. The pre-generation unit 13 outputs, from the feature point extraction unit 10, coordinates of at least one of the feature points from the feature point 201 to the feature point 207 predetermined along the skeleton of the subject image 200 (entire body) of the input image 100 (step S101).

The pre-generation unit 13 acquires coordinates of the subject frame 208 (first subject frame), which is a frame surrounding the subject image 200 in the input image 100, from the coordinate estimation unit 11 (step S102).

The pre-generation unit 13 determines whether all feature point coordinates predetermined along the skeleton of the subject image 200 have been acquired (step S103). When it is determined that any of the feature point coordinates is not acquired (step S103: NO), the pre-generation unit 13 ends the processing illustrated in FIG. 12.

When it is determined that all the feature point coordinates predetermined along the skeleton of the subject image 200 have been acquired (step S103: YES), the pre-generation unit 13 determines whether the coordinates of the subject frame 208 have been acquired and all the feature point coordinates exist in the subject frame 208 (step S104).

When it is determined that the coordinates of subject frame 208 have not been acquired or any feature point coordinates do not exist in the subject frame 301 (step S104: NO), the pre-generation unit 13 ends the processing illustrated in FIG. 12.

When it is determined that the coordinates of the subject frame 208 have been acquired and all the feature point coordinates exist in the subject frame 208 (step S104: YES), the pre-generation unit 13 generates the missing pattern as illustrated in FIGS. 5 and 7. The pre-generation unit 13 derives the distance addition result and the correction coefficient for each generated missing pattern (step S105).

The pre-generation unit 13 records, for each piece of subject identification data "n" as illustrated in FIG. 8, the subject frame height (correct height) of the subject frame 208 and the combination of the missing pattern, the distance addition result, and the correction coefficient are recorded in the subject data storage unit 15 (database) via the control unit 14 as missing data (step S106).

Figure 13:
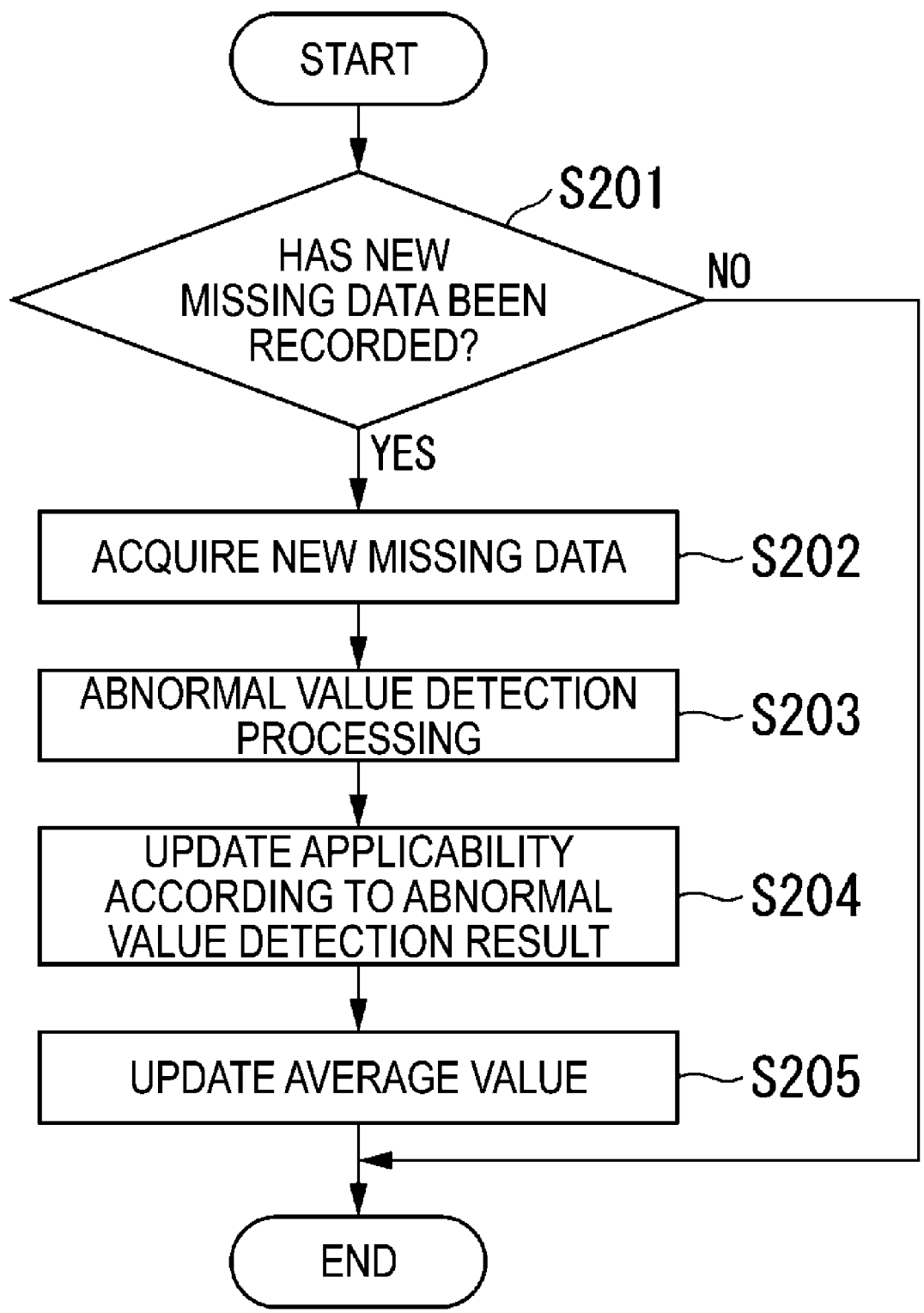
FIG. 13 is a flowchart illustrating an operation example of a control unit in the embodiment.

FIG. 13 is a flowchart illustrating an operation example of the control unit 14. The operation illustrated in FIG. 13 is performed at a stage prior to the stage of the estimation processing. The control unit 14 determines whether new missing data has been recorded in the subject data storage unit 15 (database). When it is determined that no new missing data has been recorded (step S201: NO), the control unit 14 ends the processing illustrated in FIG. 13.

When it is determined that new missing data has been recorded (step S201: YES), the control unit 14 acquires new missing data (subject identification data "n", the subject frame height of the subject frame 208, and the combination of the missing pattern, the distance addition result, and the correction coefficient) from the subject data storage unit 15 (step S202).

The control unit 14 performs processing of detecting an abnormal value in the new missing data. For example, the control unit 14 detects an element outside a predetermined range among elements of the missing data as an abnormal value. This predetermined range is determined, for example, on the basis of an average value of each element of the missing data (step S203).

According to the detection result of the abnormal value, the control unit 14 updates the applicability as illustrated in FIG. 8. For example, the control unit 14 associates missing data including elements detected as abnormal values with not applicable. For example, the control unit 14 associates missing data including elements that are not detected as abnormal values with applicable (return processing) (step S204). The control unit 14 updates the average value of the plurality of elements of the missing data. The control unit 14 records the updated average value in the subject data storage unit 15 (database) as illustrated in FIG. 8 (step S205).

Figure 14:
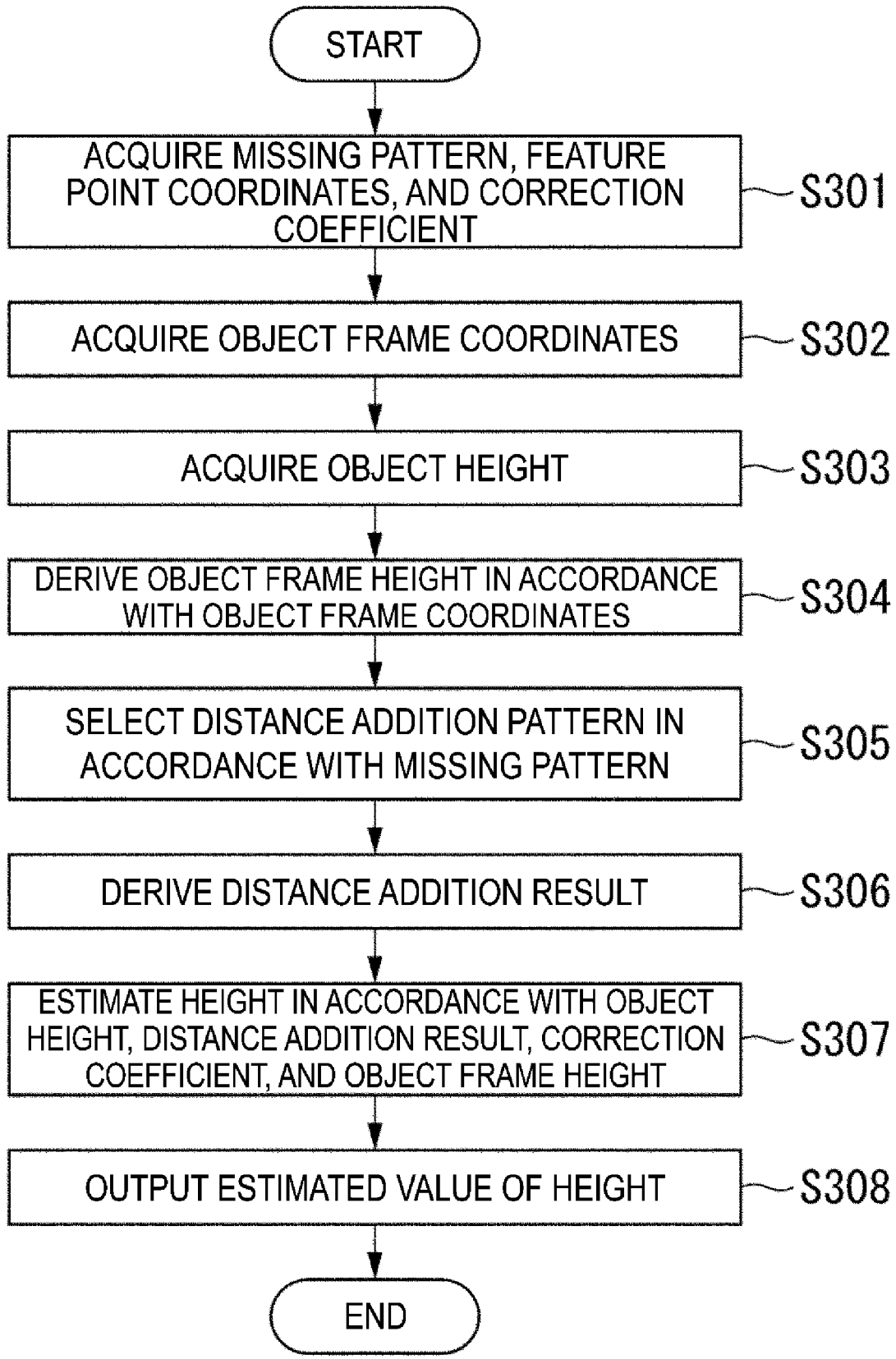
FIG. 14 is a flowchart illustrating an operation example of a height estimation unit in the embodiment.

FIG. 14 is a flowchart illustrating an operation example of the height estimation unit 20. The operation illustrated in FIG. 14 is performed at the stage of the estimation processing. The height estimation unit 20 acquires, from the subject data selection unit 17, a missing pattern of feature point coordinates in the input image 300, and the feature point coordinates and the correction coefficient selected on the basis of the missing pattern (step S301).

The height estimation unit 20 acquires, from the coordinate estimation unit 11, coordinates (object frame coordinates) of the object frame 401 in the input image 300 (step S302). The height estimation unit 20 acquires, from the object data selection unit 19, an object height associated with a name of an object of the object image 400 in the input image 300 (step S303).

The height estimation unit 20 derives a height (object frame height) of the object frame 401 on the basis of coordinates (object frame coordinates) of the object frame 401. For example, the height estimation unit 20 derives an absolute value of a difference between the y coordinate of the object frame origin 402 and they coordinate of the object frame maximum point 403 as the height of the object frame 401 (step S304).

The height estimation unit 20 selects an addition pattern of the distance between the feature point coordinates of the input image 300, on the basis of the missing pattern of the feature point coordinates in the input image 300. For example, since the feature point coordinates "K2" in the input image 300 are missing, when the height estimation unit 20 acquires a missing pattern "P1A" from the subject data selection unit 17, the height estimation unit 20 selects distance addition patterns "K1-K3, K3-K4, K4-K5" illustrated in FIG. 5 (step S305).

The height estimation unit 20 derives a result of adding the distance between the feature point coordinates on the basis of the distance addition pattern. For example, the height estimation unit 20 adds a Euclidean distance between the feature point coordinates "K1-K3", a Euclidean distance between the feature point coordinates "K3-K4", and a Euclidean distance between the feature point coordinates "K4-K5" on the basis of the distance addition patterns "K1-K3, K3-K4, K4-K5" (step S306).

The height estimation unit 20 estimates the height of the subject of the subject image 200 on the basis of the object height, the distance addition result, the correction coefficient, and the object frame height. That is, the height estimation unit 20 derives the estimated value of the height as in Equation (1) (step S307). The height estimation unit 20 outputs the estimated value of the height to, for example, the display unit 5 (step S308).

Figure 15:
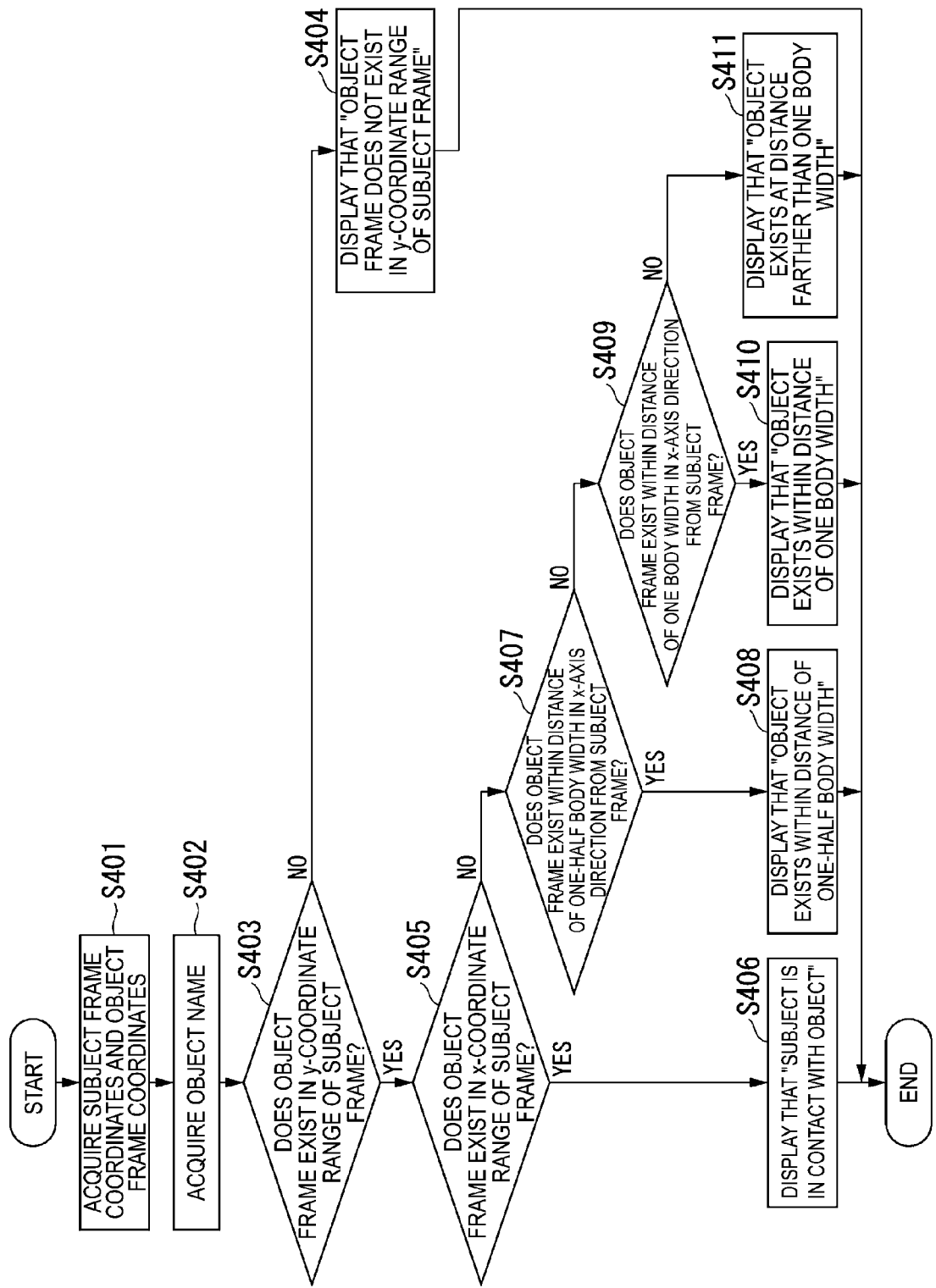
FIG. 15 is a flowchart illustrating an operation example of a display data generation unit in the embodiment.
Figure 16:
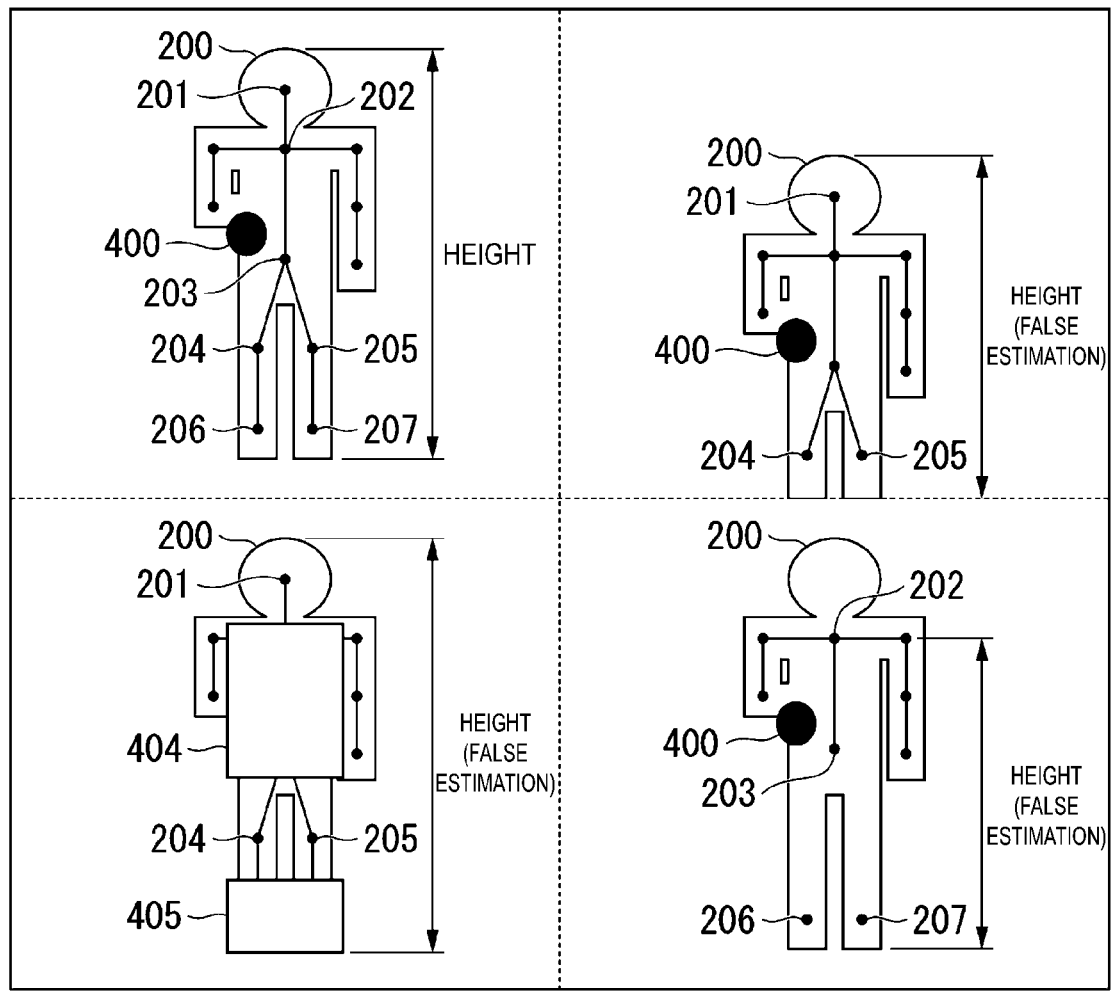
FIG. 16 is a diagram illustrating an example of an estimated height.

FIG. 15 is a flowchart illustrating an operation example of the display data generation unit 21. The operation illustrated in FIG. 15 is performed at the stage of the estimation processing. The display data generation unit 21 acquires, from the coordinate estimation unit 11, the subject frame origin 302 and the subject frame maximum point 303 in the input image 300 as coordinates of the subject frame 301. The display data generation unit 21 acquires, from the coordinate estimation unit 11, the object frame origin 402 and the object frame maximum point 403 in the input image 300 as coordinates of the object frame 401 (step S401).

The display data generation unit 21 acquires the name of the object of the object image 400 in the input image 300 from the name estimation unit 18 (step S402). The display data generation unit 21 determines whether at least a part of the y-coordinate range of the object frame 401 exists in the y-coordinate range of the subject frame 301 (step S403).

When none of the y-coordinate range of the object frame 401 exists in the y-coordinate range of the subject frame 301 (step S403: NO), the display data generation unit 21 causes the display unit 5 to display that "the object frame does not exist in the y-coordinate range of the subject frame" (step S404). The display data generation unit 21 ends the processing illustrated in FIG. 15.

When at least a part of the y-coordinate range of the object frame 401 exists in the y-coordinate range of the subject frame 301 (step S403: YES), the display data generation unit 21 determines whether at least a part of the x-coordinate range of the object frame 401 exists in the x-coordinate range of the subject frame 301 (step S405).

When it is determined that at least a part of the x-coordinate range of the object frame 401 exists in the x-coordinate range of the subject frame 301 (step S405: YES), the display data generation unit 21 causes the display unit 5 to display that "the object is in contact with the subject" (step S406). The display data generation unit 21 ends the processing illustrated in FIG. 15.

When it is determined that none of the x-coordinate range of the object frame 401 exists in the x-coordinate range of the subject frame 301 (step S405: NO), the display data generation unit 21 determines whether the object frame 401 exists within a one-half body width (half of the width of the subject frame 301 in the x-axis direction) distance in the x-axis direction from the subject frame 301 (step S407).

When it is determined that the object frame 401 exists within the distance of one-half body width in the x-axis direction from the subject frame 301 (step S407: YES), the display data generation unit 21 causes the display unit 5 to display that an object exists within the distance of one-half body width (step S408). The display data generation unit 21 ends the processing illustrated in FIG. 15.

When it is determined that the object frame 401 does not exist within the distance of one-half body width in the x-axis direction from the subject frame 301 (step S407: NO), the display data generation unit 21 determines whether the object frame 401 exists within a distance of one body width (the width of the subject frame 301 in the x-axis direction) distance in the x-axis direction from the subject frame 301 (step S409).

When it is determined that the object frame 401 exists within the distance of one body width in the x-axis direction from the subject frame 301 (step S409: YES), the display data generation unit 21 causes the display unit 5 to display that an object exists within the distance of one body width (step S410). The display data generation unit 21 ends the processing illustrated in FIG. 15.

When it is determined that the object frame 401 does not exist within the distance of one body width in the x-axis direction from the subject frame 301 (step S409: NO), the display data generation unit 21 causes the display unit 5 to display that an object exists at a distance more than the distance of one body width (step S411). The display data generation unit 21 ends the processing illustrated in FIG. 15.

As described above, at a stage prior to the stage of the estimation processing, the feature point extraction unit 10 (first feature point extraction unit) extracts feature point coordinates (coordinates of each feature point from the feature point 201 to the feature point 207) that are coordinates of each feature point predetermined along the skeleton of the subject image 200 from the input image 100 (first input image) in which the subject image 200 is captured. The coordinate estimation unit 11 (first coordinate estimation unit) estimates coordinates of a subject frame 208 that is a frame surrounding the subject image 200 in the input image 100. Pre-generation unit 13 derives the height (correct height) of subject frame 208 in the input image 100 on the basis of the coordinates (subject frame origin 209 and subject frame maximum point 210) of the subject frame 208. The pre-generation unit 13 generates a distance addition pattern, which is an addition pattern of distances between the feature point coordinates, for each missing pattern, which is a pattern of a combination of one or more feature point coordinates not extracted among predetermined feature point coordinates and a correction coefficient.

At the stage of the estimation processing, the feature point extraction unit 10 (second feature point extraction unit) extracts feature point coordinates (coordinates of at least one feature point among the feature points from the feature point 201 to the feature point 207) from the input image 300 (second input image) in which the object image 400 and the subject image 200 are captured. The coordinate estimation unit 11 (second coordinate estimation unit) estimates coordinates of the subject frame 301 (second subject frame), which is a frame surrounding the subject image 200 in the input image 300, and estimates coordinates of the object frame 401, which is a frame surrounding the object image 400 in the input image 300. The subject data selection unit 17 selects, on the basis of each feature point coordinate extracted from the input image 300, a missing pattern of each feature point and a correction coefficient that is a coefficient for correcting an estimated value of a height of the subject.

At the stage of the estimation processing, the object data selection unit 19 acquires information (object name) related to the object image 400 in the input image 300 from the name estimation unit 18. The object data selection unit 19 performs the collation processing using the information on the object image 400. That is, the object data selection unit 19 selects the object height (correct height) which is the height of the object in the object image 400 captured in the input image 300 on the basis of the information regarding the object image 400 in the input image 300.

At the stage of the estimation processing, the height estimation unit 20 adds the distance between the feature point coordinates extracted from the input image 300 on the basis of the selected missing pattern. That is, the height estimation unit 20 adds the distance between the extracted feature point coordinates on the basis of a distance addition pattern associated with the selected missing pattern. The height estimation unit 20 derives an estimated value of the height of the subject of the subject image 200 on the basis of the result of adding the distance between the feature point coordinates in the input image 300, the correction coefficient selected by the subject data selection unit 17, the object height acquired from the name estimation unit 18, and the coordinates of the object frame 401.

As described above, the height estimation unit 20 derives an estimated value of the height of the subject of the subject image 200 on the basis of the result of adding the distance between the feature point coordinates in the input image 300, the correction coefficient selected by the subject data selection unit 17, the object height acquired from the name estimation unit 18, and the coordinates (height) of the object frame 401. As a result, the height estimation unit 20 can improve accuracy of estimating the height of a subject on the basis of an image even in a case where some of predetermined feature points along a skeleton of the subject is not extracted from the image. Even in a case where the subject is not captured facing the front (for example, in the case of facing sideward or backward), the height estimation unit 20 can improve the accuracy of estimating the height of the subject on the basis of the image.

Although the embodiment of the present invention has been described in detail with reference to the drawings, a specific configuration is not limited to the embodiment, and a design or the like in a range that does not depart from the gist of the present invention is included.

INDUSTRIAL APPLICABILITY

The present invention is applicable to an apparatus that estimates a height of an imaged subject.

REFERENCE SIGNS LIST

1 . . . Height estimation apparatus
2 . . . Processor
3 . . . Storage unit
4 . . . Communication unit
5 . . . Display unit
10 . . . Feature point extraction unit
11 . . . Coordinate estimation unit
13 . . . Pre-generation unit
14 . . . Control unit
15 . . . Subject data storage unit
16 . . . Object data storage unit
17 . . . Subject data selection unit
18 . . . Name estimation unit
19 . . . Object data selection unit
20 . . . Height estimation unit
21 . . . Display data generation unit
100 . . . Input image
101 . . . Input image origin
102 . . . Input image maximum point
200 . . . Subject image
201 . . . Feature point
202 . . . Feature point
203 . . . Feature point
204 . . . Feature point
205 . . . Feature point
206 . . . Feature point
207 . . . Feature point
208 . . . Subject frame 209 . . . Subject frame origin
210 . . . Subject frame maximum point
300 . . . Input image
301 . . . Subject frame
302 . . . Subject frame origin
303 . . . Subject frame maximum point
304 . . . Input image origin
305 . . . Input image maximum point
400 . . . Object image
401 . . . Object frame
402 . . . Object frame origin
403 . . . Object frame maximum point
404 . . . Object
405 . . . Obstacle

The invention claimed is:

1. A height estimation method performed by a height estimation apparatus, the method comprising:
   extracting, from a first input image in which a subject image that is an image of a subject is captured, a feature point coordinate that is a coordinate of a feature point predetermined along a skeleton of the subject image;
   estimating a coordinate of a first subject frame that is a frame surrounding the subject image in the first input image;
   deriving a height of the first subject frame in the first input image in accordance with the coordinate of the first subject frame and generating a distance addition pattern that is an addition pattern of a distance between a feature point coordinate and another feature point coordinate and a correction coefficient for an individual missing pattern that is a pattern of a combination of one or a plurality of the feature point coordinates that are not extracted among the plurality of the feature point coordinates predetermined;
   extracting a feature point coordinate from a second input image in which an object image that is an image of an object and the subject image are captured;
   estimating a coordinate of a second subject frame that is a frame surrounding the subject image in the second input image and estimating a coordinate of an object frame that is a frame surrounding the object image in the second input image;
   selecting the individual missing pattern and the correction coefficient in accordance with the feature point coordinate extracted from the second input image;
   selecting an object height that is a height of the object in the object image in the second input image in accordance with information on the object image in the second input image; and
   adding up a distance between a feature point coordinate and another feature point coordinate extracted from the second input image in accordance with the missing pattern selected and deriving an estimated value of a height of the subject in accordance with a result of adding up the distance between the feature point coordinate and the other feature point coordinate in the second input image, the correction coefficient selected, the object height, and the coordinate of the object frame.

2. The height estimation method according to claim 1, comprising
   displaying a distance between the subject and the object.

3. A non-transitory computer-readable medium having computer-executable instructions that, upon execution of the instructions by a processor of a computer, cause the computer to function as the height estimation method according to claim 1.

4. A height estimation apparatus comprising:
   a processor; and
   a storage medium having computer program instructions stored thereon, when executed by the processor, perform to:
   extract, from a first input image in which a subject image that is an image of a subject is captured, a feature point coordinate that is a coordinate of a feature point predetermined along a skeleton of the subject image;
   estimate a coordinate of a first subject frame that is a frame surrounding the subject image in the first input image;
   derive a height of the first subject frame in the first input image in accordance with the coordinates of the first subject frame, and generate a distance addition pattern that is an addition pattern of a distance between a feature point coordinate and another feature point coordinate and a correction coefficient for an individual missing pattern that is a pattern of a combination of one or a plurality of the feature point coordinates that are not extracted among the plurality of the feature point coordinates predetermined;
   extract a feature point coordinate from a second input image in which an object image that is an image of an object and the subject image are captured;
   estimate a coordinate of a second subject frame that is a frame surrounding the subject image in the second input image and estimate a coordinate of an object frame that is a frame surrounding the object image in the second input image;
   select the individual missing pattern and the correction coefficient in accordance with the feature point coordinate extracted from the second input image;
   select an object height that is a height of the object in the object image in the second input image in accordance with information on the object image in the second input image; and
   add up a distance between a feature point coordinate and another feature point coordinate extracted from the second input image in accordance with the missing pattern selected and derive an estimated value of a height of the subject in accordance with a result of adding up the distance between the feature point coordinate and the other feature point coordinate in the second input image, the correction coefficient selected, the object height, and the coordinate of the object frame.

* * * * *